(12) United States Patent  (10) Patent No.: US 7,845,353 B2
Bordewick et al. (45) Date of Patent: Dec. 7, 2010

(54) FACE MASK SUPPORT

(75) Inventors: Steven S. Bordewick, Minneapolis, MN (US); Bruce Bowman, Eden Prairie, MN (US); David Markovich, Eden Prairie, MN (US); Laurel D. Brandt, Eagan, MN (US); Mark J. Weimholt, Coon Rapids, MN (US); Amy Raatikka, Maple Grove, MN (US)

(73) Assignee: AEIOMed, Inc., Minneapolis, MN (US)

( * ) Notice: Subject to any disclaimer, the term of this patent is extended or adjusted under 35 U.S.C. 154(b) by 292 days.

(21) Appl. No.: 11/805,161

(22) Filed: May 21, 2007

(65) Prior Publication Data

US 2008/0053451 A1  Mar. 6, 2008

Related U.S. Application Data

(63) Continuation-in-part of application No. 11/455,544, filed on Jun. 19, 2006, which is a continuation of application No. 11/056,858, filed on Feb. 12, 2005, now Pat. No. 7,089,941, which is a continuation-in-part of application No. 10/643,642, filed on Aug. 19, 2003, now Pat. No. 6,854,465.

(60) Provisional application No. 60/619,539, filed on Oct. 15, 2004, provisional application No. 60/404,685, filed on Aug. 20, 2002.

(51) Int. Cl.
 *A62B 18/02* (2006.01)
(52) U.S. Cl. ............... 128/207.11; 128/207.13; 128/207.17; 128/205.25; 128/206.12; 128/206.18; 128/206.21; 128/206.27; 128/206.28; 128/201.22; 128/201.23; 128/201.24; 2/410; 2/5; 2/6.1; 2/6.2; 2/6.6; 2/6.8; 2/417; 2/418; 2/421; 2/422; 2/424

(58) Field of Classification Search ............ 128/207.11, 128/207.13, 207.17, 205.25, 206.12, 206.18, 128/206.21, 206.27, 206.28, 201.22, 201.23, 128/201.24; 2/410, 5, 6.1, 6.2, 6.6, 6.8, 417, 2/418, 421, 422, 424, 9, 171, 173, 202, 205, 2/206, 209, 908, 909, 912
See application file for complete search history.

(56) References Cited

U.S. PATENT DOCUMENTS

| 1,081,745 A | 12/1913 | Johnston et al. |
| 1,282,527 A | 10/1918 | Bidonde |
| 1,632,449 A | 6/1927 | McKesson |

(Continued)

FOREIGN PATENT DOCUMENTS

EP  1 334 742 B1  8/2003

(Continued)

*Primary Examiner*—Patricia M Bianco
*Assistant Examiner*—Nihir Patel
(74) *Attorney, Agent, or Firm*—Clise, Billion & Cyr, P.A.

(57) ABSTRACT

Mask apparatus and methods for providing positive airway pressure therapies are disclosed. The mask apparatus includes a mask secured to the mount with the mask cantilevered from the mount. A circumferential band, a first lateral stabilizing band and a second lateral stabilizing band secure the mount to the head of a user. The methods include securing a mask apparatus to the head of a user and administering a positive airway pressure therapy.

4 Claims, 10 Drawing Sheets

U.S. PATENT DOCUMENTS

| | | | |
|---|---|---|---|
| 2,241,535 A | 5/1941 | Boothby et al. | |
| 2,965,902 A | 12/1960 | Louch | |
| 3,599,635 A | 8/1971 | Ansite | |
| 3,721,233 A | 3/1973 | Montgomery et al. | |
| 3,799,164 A | 3/1974 | Rollins | |
| 4,151,843 A | 5/1979 | Brekke et al. | |
| 4,593,688 A | 6/1986 | Payton | |
| 4,644,947 A | 2/1987 | Whitwam et al. | |
| 4,944,310 A | 7/1990 | Sullivan | |
| 5,054,484 A | 10/1991 | Hebeler, Jr. | |
| 5,421,799 A | 6/1995 | Rabin et al. | |
| 5,538,000 A | 7/1996 | Rudolph | |
| 5,542,128 A | 8/1996 | Lomas | |
| 5,623,923 A | 4/1997 | Bertheau et al. | |
| 5,662,101 A * | 9/1997 | Ogden et al. | 128/205.25 |
| 5,687,715 A | 11/1997 | Landis et al. | |
| 5,724,965 A | 3/1998 | Handke et al. | |
| 5,954,050 A | 9/1999 | Christopher | |
| 6,119,693 A | 9/2000 | Kwok et al. | |
| 6,347,631 B1 | 2/2002 | Hansen et al. | |
| 6,494,207 B1 | 12/2002 | Kwok | |
| 6,505,623 B1 | 1/2003 | Hansen | |
| 6,516,802 B2 | 2/2003 | Hansen et al. | |
| 6,530,373 B1 | 3/2003 | Patron et al. | |
| 6,532,960 B1 | 3/2003 | Yurko | |
| 6,536,435 B1 | 3/2003 | Fecteau et al. | |
| 6,694,978 B1 | 2/2004 | Bennarsten | |
| 6,789,543 B2 | 9/2004 | Cannon | |
| 6,854,465 B2 | 2/2005 | Bordewick et al. | |
| 6,886,564 B2 | 5/2005 | Sullivan et al. | |
| 7,089,941 B2 | 8/2006 | Bordewick et al. | |
| 7,156,090 B2 | 1/2007 | Nomori | |
| 7,357,136 B2 | 4/2008 | Ho et al. | |
| 7,487,778 B2 | 2/2009 | Freitag | |
| 7,588,033 B2 | 9/2009 | Wondka | |
| 2002/0011248 A1 | 1/2002 | Hansen et al. | |
| 2003/0051732 A1 | 3/2003 | Smith et al. | |
| 2003/0172936 A1 | 9/2003 | Wilkie et al. | |
| 2004/0025882 A1 | 2/2004 | Madaus et al. | |
| 2004/0035427 A1 | 2/2004 | Bordewick et al. | |
| 2004/0226562 A1 | 11/2004 | Bordewick | |
| 2004/0226566 A1 | 11/2004 | Gunaratnam et al. | |
| 2005/0150499 A1 | 7/2005 | Bordewick et al. | |
| 2006/0231097 A1 | 10/2006 | Dougherty et al. | |
| 2006/0231102 A1 | 10/2006 | Bordewick et al. | |
| 2007/0277825 A1 | 12/2007 | Bordewick et al. | |
| 2007/0277827 A1 | 12/2007 | Bordewick et al. | |
| 2008/0006275 A1 | 1/2008 | Nickelson et al. | |
| 2008/0053451 A1 | 3/2008 | Bordewick et al. | |

FOREIGN PATENT DOCUMENTS

| | | |
|---|---|---|
| WO | WO 2004/012803 A1 | 2/2004 |
| WO | WO 2006/044120 A2 | 4/2006 |

\* cited by examiner

FACE MASK SUPPORT

CROSS REFERENCE TO RELATED APPLICATIONS

The present application is a continuation-in-part of U.S. patent application Ser. No. 11/455,544, filed Jun. 19, 2006 which is a continuation of U.S. patent application Ser. No. 11/056,858, filed Feb. 12, 2005 now issued as U.S. Pat. No. 7,089,941 which claims the benefit of U.S. Provisional Application Ser. No. 60/619,539, filed on Oct. 15, 2004 and which is a continuation-in-part of U.S. patent application Ser. No. 10/643,642, filed Aug. 19, 2003, now issued as U.S. Pat. No. 6,854,465 which claims the benefit of U.S. Provisional Application Ser. No. 60/404,685 filed Aug. 20, 2002. All of the preceding patents and patent applications are incorporated herein by reference in their entirety.

BACKGROUND OF THE INVENTION

1. Summary of the Invention

The present inventions relate generally to pressurized respiratory therapy and, more particularly, to face mask supports for providing pressurized gas to the airways of a user.

2. Description of the Related Art

Airway patency may be related to a number of sleep related disorders, including snoring and sleep apnea for example. As a person ages, airway patency may be reduced due to loss of muscle tone in the muscles of the throat which normally serve to prevent the tissues from impinging on the airway. This condition may be more severe in patients who are obese, have naturally narrow airways or airways that may be partially blocked by tonsils, soft palate or uvula. One result can be snoring as the tissues vibrate as air may be forced through the narrowed airway under heightened pressure. Snoring may be disruptive to sleep; for the snorer not only keeps companions awake but will himself awaken many times in the night. This sleep disturbance can lead to feelings of tiredness or exhaustion during the day and a decrease in mental and physical performance.

In certain situations, the condition can be lethal. When narrowing of the airway proceeds to complete occlusion, the condition is commonly termed sleep apnea. A faulty feedback loop between the brain and the respiratory system lets the airway completely collapse until the brain registers low oxygen levels, high carbon dioxide levels or labored breathing, and the user awakens to resume breathing. These constant jump starts, which can happen as often as once a minute or more, cause an erratic heart rate and fluctuating blood pressure. In susceptible patients, this condition can lead to cardiovascular death.

Continuous positive airway pressure (CPAP), as well as other positive airway pressure therapies, may be used to alleviate the symptoms of snoring or sleep apnea by delivering air or gas under a pressure sufficient to mimic the effect of the natural waking tone of the throat muscles in holding the soft tissues around the airway from partially or totally occluding the airway passage.

Patients, other than those with airway problems, can also benefit from positive airway pressure therapies. This include patients with weakened respiratory muscles who cannot pull air into their lungs, such as those with post polio or amyotrophic lateral sclerosis disease, patients with traumatic nerve damage or adult respiratory distress.

Positive airway pressure apparatus are generally comprised of a blower for providing a stream of air or gas under pressure, a mask, and tubing to connect the mask to the blower source. The mask can cover both the mouth and nose, the nose alone, have plugs that insert only into the nares, or a mouthpiece in the mouth. Whatever the configuration, the mask must have, as a minimum, a means of sealing the mask to the face so that the blower gas does not escape, thereby reducing the pressure to the airway. Vents must be provided for exhaled gases. Preferably the vents are placed so as to avoid the eyes of the user. A mask support may be necessary to hold the mask and tubing in proper apposition.

User compliance with positive airway pressure therapies is sometimes a problem. Many of the masks currently available are uncomfortable, tend to be dislodged during sleep or disconnected from the blower source. Prior face mask systems have included straps that extended across the face of a user to provide a tension to a mask to assist in sealing the mask. Such straps frequently cause user discomfort and can contribute to a user's in compliance with the recommended therapy.

If the mask is a full face mask covering both nose and mouth or a nasal mask covering only the nose, the peripheries of the mask will touch the bridge of the nose, the upper or lower lip and must seal around the malar region. Individual variations in the topography, especially of the malar region, make it necessary to hold the mask to the face with some pressure. It has been shown that a double seal, with a semi-rigid internal support and a flexible skirt can be inflated with air, forming a seal that more readily conforms to the malar region. The ideal mask support may be usable with any variety of full face, nasal, or oral masks to accommodate individual needs and preferences.

Accordingly, a need exists for a mask support that may be comfortable, does not apply pressure to small or sensitive areas of the head and may be not easily dislodged or disconnected from its blower source.

SUMMARY OF THE INVENTION

Apparatus and methods in accordance with the present invention may resolve many of the needs and shortcomings discussed above and will provide additional improvements and advantages as will be recognized by those skilled in the art upon review of the present disclosure.

The present invention provides a mask apparatus for delivering positive airway pressure therapies. The mask apparatus may include a mount, a mask, a circumferential band, a first lateral stabilizing band and a second lateral stabilizing band. The mask may be secured to the mount with the mask cantilevered from the mount. The circumferential band may also be secured to the mount. The first lateral stabilizing band and a second lateral stabilizing band each include a first end and a second end. In one aspect, the first end of the first lateral stabilizing band may be secured to the mount and the second end of the first lateral stabilizing band may be secured to the circumferential band. Similarly, the first end of the second lateral stabilizing band may be secured to the mount and the second end of the second lateral stabilizing band may be secured to the circumferential band. In another aspect, the first end of the first lateral stabilizing band may be secured to the mount and the first end of the second lateral stabilizing band may be secured to the mount. In this aspect, the second end of the first lateral stabilizing band may be secured to or integral with the second end of the second lateral stabilizing band such that the first lateral stabilizing band and the second lateral stabilizing band may extend circumferentially about at least a portion of the head of a user.

Other features and advantages of the invention will become apparent to those skilled in the art upon review of the following detailed description, and from the claims.

All Figures are illustrated for ease of explanation of the basic teachings of the present invention only; the extensions of the Figures with respect to number, position, relationship and dimensions of the parts to form the embodiment will be explained or will be within the skill of the art after the following description has been read and understood. Further, the exact dimensions and dimensional proportions to conform to specific force, weight, strength, flow and similar requirements will likewise be within the skill of the art after the following description has been read and understood.

Where used in various Figures of the drawings, the same numerals designate the same or similar parts. Furthermore, when the terms "top," "bottom," "right," "left," "forward," "rear," "first," "second," "inside," "outside," and similar terms are used, the terms should be understood to reference only the structure shown in the drawings and utilized only to facilitate describing the illustrated embodiments. Similarly, when the terms "proximal," "distal," "anterior," "posterior," "medial," "lateral" "superior," "inferior," and similar positional terms are used, the terms should be understood to reference the structures shown in the drawings relative to a user using the illustrated apparatus.

DETAILED DESCRIPTION OF THE INVENTION

The present inventions provide mask apparatus 10 and associated methods for use in conjunction with positive pressure airway therapies. The mask apparatus 10 include a plurality of stabilizing bands 12 and a mount 14. A mask 16 may be secured relative to the mount 14. The mount 14 may be secured to the head of a user by one or more bands 12 to secure the mask 16 in communication with airway of the user. Typically, the bands 12 and mount 14 are configured to bias the mask 16 against aspects of the user's face to form a seal between the mask 16 and the face sufficient to permit the administering of a positive pressure therapy to the user. The mask 16 is cantilevered from the mount 14 and configured to exert a sealing force against the face of a user to eliminate the need for bands extending over the sensitive portions of face below the forehead and eyebrows.

When used in this patent application, the following terms have the following meaning:

"Air" is used to denote a gas to be delivered to a user and includes atmospheric gas, oxygen, other gases or combinations of these gases.

"Crown of the head" refers to the area of the head past the vertical plane of the forehead, that is, the top of the head.

"Hair line" refers to highest area of the forehead, whether or not hair may be present.

"Bias" means to press one surface against another.

"Mask" refers to any device for linking a positive pressure system (blower) to the airway of a user in certain embodiments, a mask 16 may cover the full face, the nose and mouth, or only the nose, may seal over or within the nares of the nose or seal in the mouth.

The Figures generally illustrate various embodiments of mask apparatus 10 including aspects of the present inventions. The particular exemplary embodiments of the mask apparatus 10 illustrated in the figures have been chosen for ease of explanation and understanding of various aspects of the present inventions. These illustrated embodiments are not meant to limit the scope of coverage but instead to assist in understanding the context of the language used in this specification and the appended claims. Accordingly, variations of mask apparatus 10 for use in administering positive pressure respiratory therapies different from the illustrated embodiments may be encompassed by the appended claims.

As generally illustrated throughout the Figures, the mask apparatus 10 includes a plurality of support bands 12 and a mount 14. The support bands 12 include at least a circumferential band 22, a first lateral stabilizing band 32 and a second lateral stabilizing band 42. Each band 12 may be secured to the mount 14. The circumferential band 22 may be configured to extend around the head of a user. A portion of the mount 14 may be secured to the circumferential band 22. A first lateral stabilizing band 32 and a second lateral stabilizing band 42 extend between the circumferential band 22 and the mount 14. The bands 12 are generally configured to secure the relative position of the mount 14 on the head of a user.

One or more of the bands 12 may have adjustable lengths to permit the proper fitting of the mask apparatus 10 to a user. The bands 12 and the mount 14 may be generally configured to secure the mount 14 in a medial position on the head of a user. The position is typically superior to the nose of the user. The mask 16 or portions of mask 16 may be secured relative to the mount 14 and extend from an anterior edge 64 of the mount 14. In certain aspects, the mask 16 may be cantilevered from the mount 14. The distance that the mask may be cantilevered from the anterior edge 64 of the mount 14 may be adjustable for proper fitment or otherwise. Similarly, the relative angle of the mount 14 and the mask 16 may also be adjustable for proper fitting and sealing. The cantilevering of the mask 16 from the mount 14 may be configured to exert a force in tension or about a fulcrum to properly seal the mask 16 against the user to permit the administration of a positive pressure therapy. A support 18 may also secure the mask 16 to the mount 14. The support 18 may be generally configured to at least in part, confer a force between the mount 14 and/or plurality of bands 12 and the mask 16. A tube 20 may be provided to communicate a supply of pressurized air to the mask 16. The tube 20 may be secured at one or more locations to the mount 14.

The mount 14 is generally configured to provide a stable structure to which the mask 16 is mounted. In certain aspects, the mask 16 is cantilevered from the mount 14. The structure of the mount 14 may be unitary or composite. Portions of mask 16 may be rigid formed from a rigid or substantially rigid material while other portions are formed from a compliant material as will be recognized by those skilled in the art upon review of the present disclosure. Various stiffening or shaping wires may also be integrated into the mask or secured to the mask as necessary for particular application or fitment of the mask 16. A lower surface 24 of the mount 14 may be configured to conform to the shape of a portion of the head of the user. An upper surface 34 of the mount 14 may be configured to secure a portion of the mask 16, a support 18 and/or a tube 20. The mount 14 defines an anterior edge 64 from which the mask 16 or portions of the mask 16 may extend. The mount 14 may include a base 74 secured to at least a portion of the lower surface of the mount 14. In certain aspects, the base 74 may provide a cushion between the mount 14 and the head of a user. In other aspects, the base 74 may provide a structural member which is connected to or integral with the bands 12 to receive a force exerted by the bands 12. In other aspects, the base 74 may function both as a structural member and a cushion. In yet other aspects, the base 74 may function as a frictional element. Those skilled in the art may recognize additional functions for a base 74 upon review of the present disclosure.

The bands 12 are typically in the form of elongated members that are configured to exert sufficient tension to retain the mask apparatus 10 on the head of a user and, more particularly, to retain the mask 16 over the airway of a user as the user sleeps. In certain aspects, the bands 12 are configured as flattened straps to comfortably distribute a force over their surface area. The bands 16 may be formed from one or more stretchable elastic materials, substantially unstretchable material, or other materials as will be recognized by those skilled in the art upon review of the present disclosure. The bands 12 may be integrally formed or interconnected by a variety of mechanical linkages. The bands 12 may incorporate various buckles, snaps, hook and loop type fasteners, such as that sold under the trade name Velcro®, or other components to link and/or permit relative adjustment of the bands 12. Various aspects of the bands 12 may be adjustable by a user. These aspects may include length, relative positions or other aspects as will be recognized by those skilled in the art upon review of the present disclosure.

The circumferential band 22 is generally configured to extend about at least a portion of the circumference of a user's head. The circumferential band 22 may be a unitary or a composite member. When configured as a composite member, one or more bands 12 may be linked to form the circumferential band 22. The circumferential band 22 may include an anterior portion 62 configured to be positioned on an anterior location of a user's head. The circumferential band 22 may also include a posterior portion 72 configured to extend about a posterior region of a user's head. In certain aspects, the posterior portion 72 may be configured as a unitary structure. The unitary structure may consist solely of a compliant material. This structure may be devoid of hard components that may create pressure points and discomfort as a user sleeps. In certain aspects, the mount 14 may be secured to the circumferential band 22 at a location on the anterior portion 62 of the circumferential band 22. The circumferential band 22 may be continuous about its circumference, may define a first end 82 and a second end 92, or may be otherwise configured as will be recognized by those skilled in the art upon review of the present disclosure. When the circumferential band 22 defines a first end 82 and a second end 92, the first end 82 and the second end 92 may be secured to one another, secured to aspects of the mount 14, or may be otherwise configured to secure the circumferential band 22 about at least a portion of the circumference of a user's head. In certain aspects, the mount 14 may be secured to the circumferential band 22 at an anterior portion 62 of the circumferential band 32. An angle 102 may be formed between the anterior portion 62 and the posterior portion 72 of the circumferential band. In certain aspects, the angle 102 may be formed as a curve in the circumferential band 22 or in a lower edge of the circumferential band to prevent irritating contact with aspects of the ear of a user. In other aspects, the angle 102 may be formed to direct the one or more forces exerted by the circumferential band 22 to at least assist in holding the apparatus 10 in place on the head of a user.

The first lateral stabilizing band 32 and the second lateral stabilizing band 42 are generally configured to stabilize the mount 14 on the head of a user. The first lateral stabilizing band 32 and the second lateral stabilizing band 42 each define at least a first end and a second end. The first lateral stabilizing band 32 and the second lateral stabilizing band 42 may be integral or may be secured to the circumferential band 22 at their first ends. The second ends of each of the first lateral stabilizing band 32 and the second lateral stabilizing band 42 may be secured to the mount 14. In one aspect, the second ends of the first lateral stabilizing band 32 and the second lateral stabilizing band 42 may be attached toward or at the posterior end 54 of the mount 14.

The mask 16 is generally configured to communicate pressurized air to the airway of a user. The mask 16 is secured to the mount 14. The mask 16 may be configured as a face mask, a nose mask, a pair of nares seals, a mouthpiece, or otherwise as will be recognized by those skilled in the art upon review of the present disclosure. The mask 16 generally includes a passage, an air outlet and one or more seals. In certain aspects, the air outlet and the seals may be formed from corresponding structure. The passage is defined by the mask 16 and is configured to receive pressurized air from a blower and may be configured to receive a tube 20 or to be received by a tube 20. The air outlet is defined by the mask and/or the seal(s) 46 of the mask 16. The air outlet is configured to communicate air from the passage to the airway of a user. The seal 46 or seals 46 are configured to abut a portion of the face of a user to provide a sufficient seal that pressurized air may be provided through the passage and received within the airway of a user from the air outlet of the mask 16.

In certain aspects, the mask 16 is cantilevered from a leading edge 64 of the mount 14. The mask 16 may include one or more rigid portions to permit the mask 16 to exert sufficient force against the face or portion thereof of the user to seal the mask 16 against the user to permit the administration of a positive pressure therapy. The mask 16 may be secured directly to the mount 14, may be secured to the mount 14 with a support 18, or may be otherwise secured as will be recognized by those skilled in the art upon review of the present disclosure. Depending on the particular configuration, the mask 16 may exert a force about a moment arm extending from the mount 14, may be held in tension between aspects of the users face and the mount 14, may exert a combination of such forces, or may otherwise contact a user's face to permit adequate sealing for administration of a positive pressure therapy.

The tube 20 is generally configured to communicate air from a source of pressurized air, such as a blower, to the passage 26 of the mask 16. The tube 20 may be in the form of a flexible ribbed hose. The tube 20 may include various flexible and/or twistable couplers to avoid torque and tension as a user moves during sleep. An opening at a first end of the tube 20 is generally configured to communicate with the source of pressurized air. An opening at the second end of the tube 20 is generally configured to communicate pressurized air to the passage 26 of a mask 16.

Figure 1:
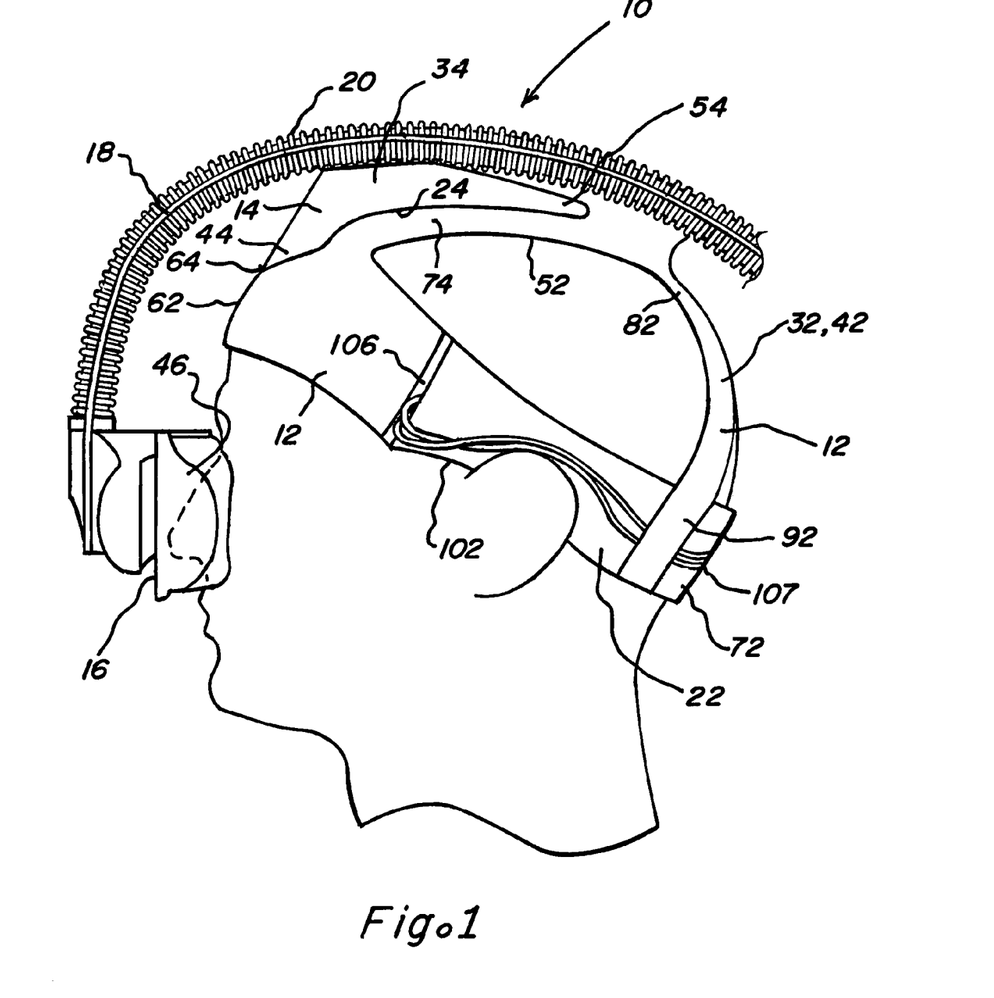
FIG. 1 illustrates a side view of an exemplary embodiment of a mask apparatus in accordance with aspects of the present inventions.
Figure 2:
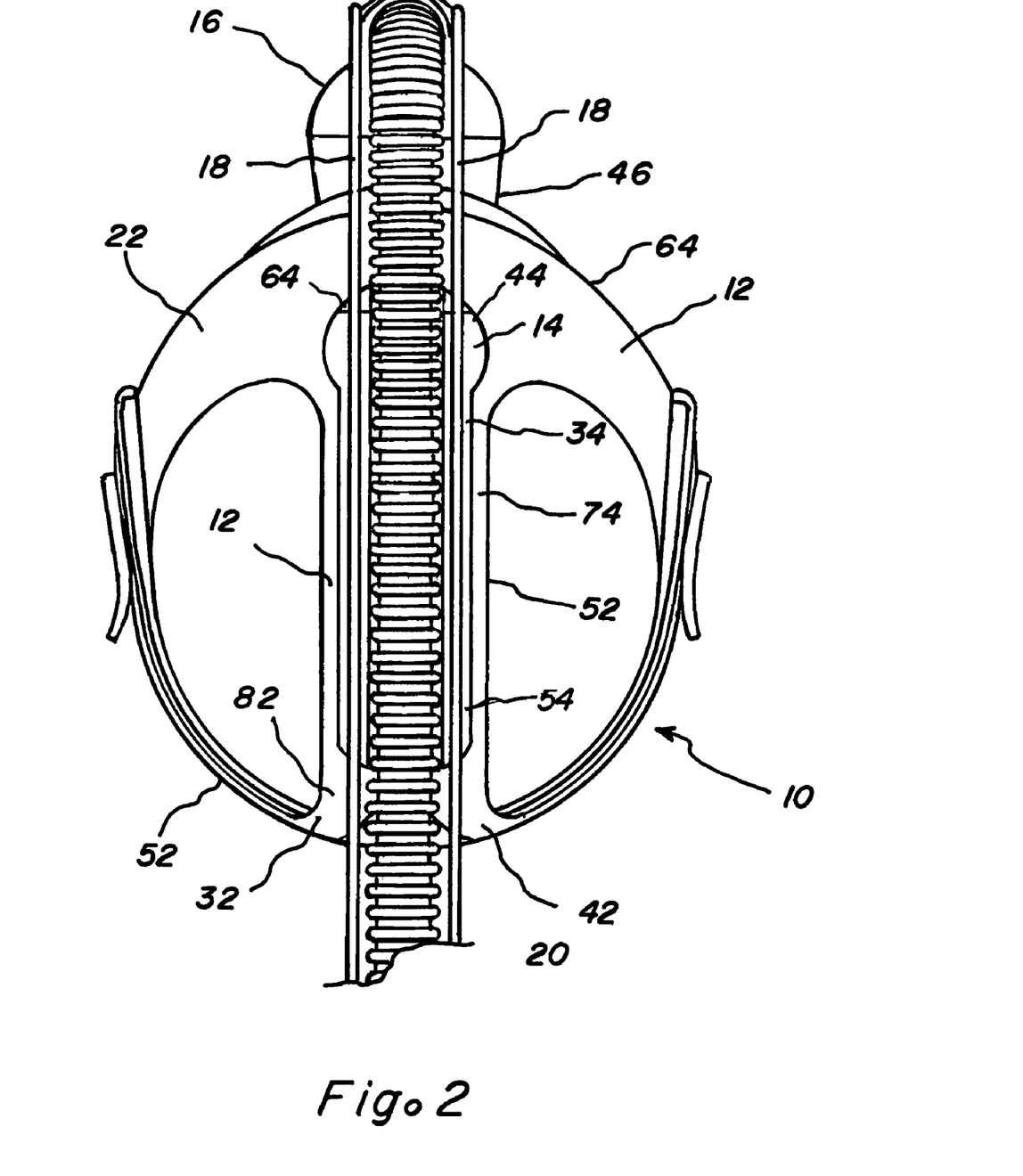
FIG. 2 illustrates a top view of an exemplary embodiment of a mask apparatus in accordance with aspects of the present inventions.

As illustrated for exemplary purposes in FIGS. 1 to 3, the circumference band 22 may extend from the middle of the forehead, avoiding the sensitive eye and eyebrow regions, to below the inion protrusion of the occipital bone (the nape of the neck). In certain aspects, this positioning may provide the desired stability to the mount 14. The circumferential band 22 may be connected to the base 74 to secure the circumferential band 22 to the anterior end 44 of the mount 14. The second ends of the first lateral stabilizing band 32 and the second lateral stabilizing band 42 are secured to the base 74 toward the posterior end 54 of the mount 14. Because the bands 12 may be sufficiently clamped, the base 74 may be sufficiently established such that it serves as a stable support for the mount 14. With the base 74 established on the medial line of the head, the mask 16 and/or support 18 may be capable of creating a counter-clockwise moment, as shown in FIG. 4, needed to keep the mask 16 biased against the face, which translates the force into a clockwise moment of the mask loading force, tending to keep the mask 16 on the face without leaking. When present, the support 18 can be configured with one or more arms and may be particularly configured with two arms as illustrated in the Figures for exemplary purposes. The arm or arms of the support 18 may be mounted to the rigid or semi-rigid mount 14 and configured to position and/or secure the mask 16 over a patient's airway. The circumferential band 22 may be fitted with adjustment means 106 and quick-sizing cord 107 to assist in fitment of the circumferential band 22 on a user's head.

Figure 3:
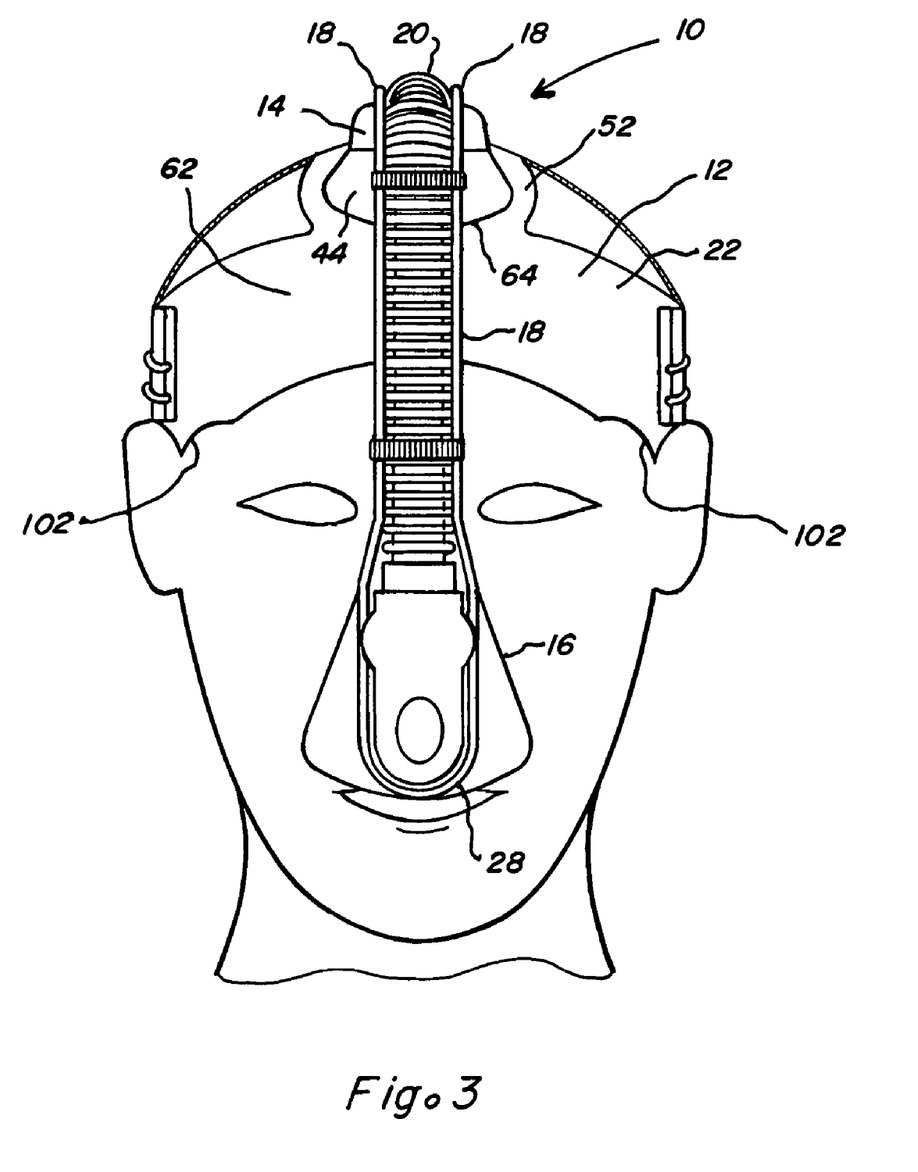
FIG. 3 illustrates a frontal view of an exemplary embodiment of a mask apparatus in accordance with aspects of the present inventions.
Figure 4:
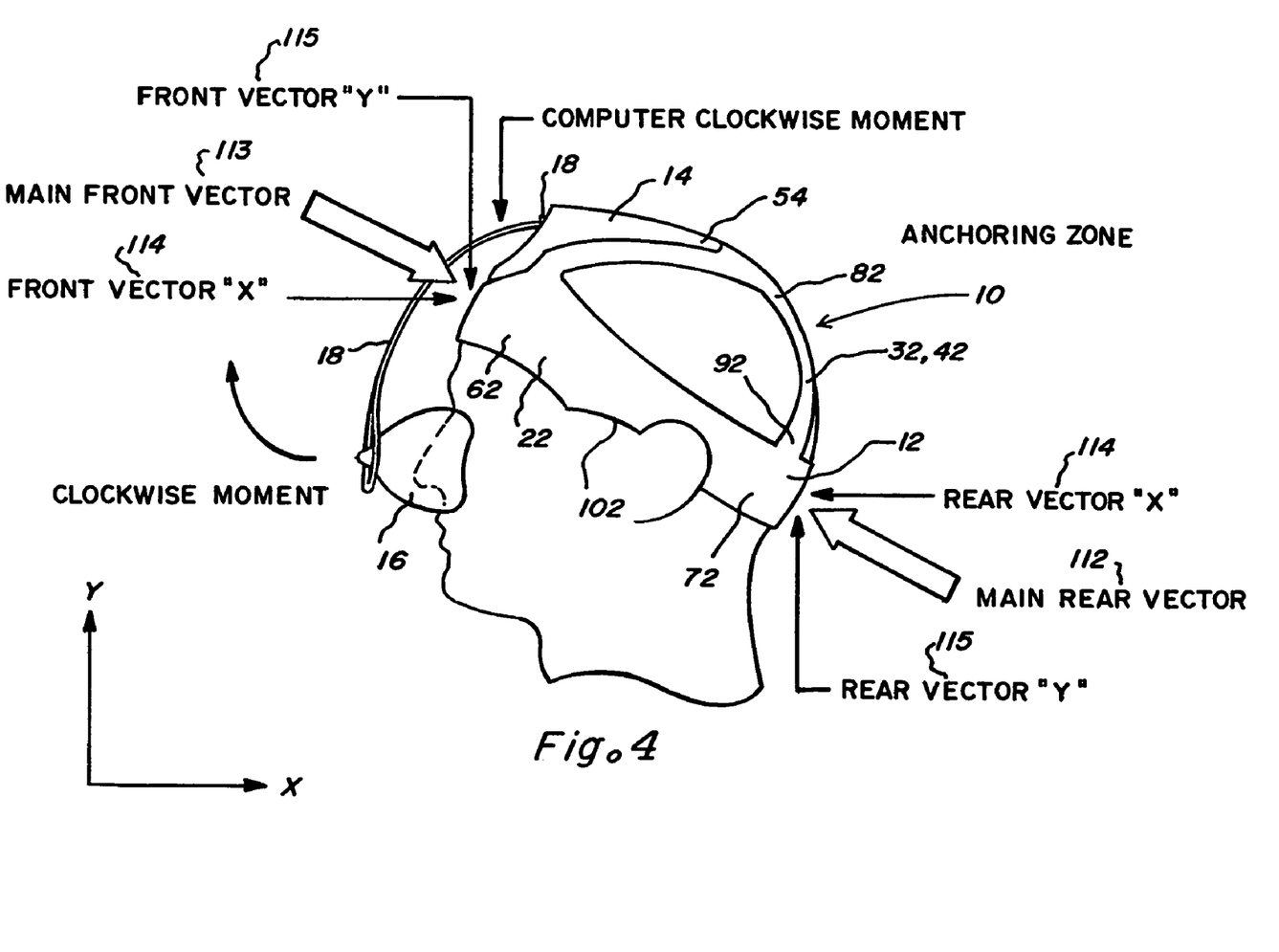
FIG. 4 illustrates exemplary force vectors on an exemplary mask apparatus in accordance with aspects of the present inventions.

As particularly illustrated in FIG. 3 for exemplary purposes, the loop 28 of the support 18 may fit around the distal surface of the mask 16. An adjustment may be provided for one or more of the mount 14, the mask 16 and the support 18. The adjustment may be in the form of a ratchet, a rotating fitting, a threaded fitted or a friction fitting, for example. The adjustment may permit the relative positioning of the mask 16 and the mount 14. The tube 20 may pass through the groove formed by the loop 28 of the support 18. The tube 20 may be secured to the support 18. At least a portion of the tube 20 may also be secured to the mount 14 or the base 74.

As particularly illustrated in FIG. 4 for exemplary purposes, the forces may be distributed between the bands 12, mount 14, mask 16 and/or support to bias the mask 16 against aspects of a user's face when worn on the head of a user. As particularly illustrated for exemplary purposes, the force may be transmitted from the top of the head to the mask 16 via the support 18. It should be noted that the force will vary from user to user. The variables may include:

the particular configuration of the mask apparatus 10;

pressure associated with the positive pressure therapy being administered;

the rate of airflow required by the user for breathing assistance;

the degree of restlessness of the user which would tend to dislodge the mask 16;

the user's personal preferences; and/or the topology of the user's face.

The biasing force may be increased or decreased by shortening or lengthening each arm of the support 18. As noted, the loading of the circumferential band 22 may be applied independently of the loading for the mask 16. The vectors created in tightening the bands 12 include the main rear vector 112 and the main front vector 113, which each occur normal to the surface of the head. The analysis of the resultant vectors X 114 and Y 115 show how the "clamping" of the head may be accomplished. Noting the vectors X and Y, it can be seen that as the various aspects of the circumferential band 22 contact the forehead at too high a position, clamping would fail because there would be no effective "undercut" for gripping and front vector X would be free to move the non rigid band back off of the head. Likewise, if the band contacts too high on the back of the head, rear vector Y would have no undercut to resist it and the bands 12 would slip upward off of the head. Once the bands 12 may be sufficiently clamped by proper positioning of the hemispheric contour, the mount 14 and/or base 74 may be held on the medial line of the head and form a stable anchor zone 116 for attachment of the mount 14. The extensive stability of the anchoring zone established by the mount 14 and/or base 74 may allow for the use of a short length of rigid or semi-rigid material comprising the mount 14. It should be noted that the mount 14 and the support 18 may be configured as the only components of the mask apparatus 10 that are not soft and flexible.

With a flexible but stable construction, the support 18 may be configured to create a counter-clockwise moment, as shown in FIG. 4 for exemplary purposes, that may keep the mask 16 biased against the face. This may translate the force into a clockwise moment of the mask loading force, tending to keep the mask 16 on the face without leaking and without the loading force being applied to a small anchor area.

In use, the user may adjust the bands 12 using the adjustment mechanism 106 to a "loose comfort" and place the cap on his or her head, positioning it from the nape of the neck to the forehead. The user then uses the quick-sizing cord 107 (on those embodiments which are provided with a quick-sizing means) to pull the bands 12 snugly around the head. The bands 12 may be adjusted for proper fitting. The bands 12 being fitted, the tube 20 from a blower may be attached to a face mask 16 so that the loop 28 of the support 18 passes around the distal protuberance of the mask 16. The ends of the support 18 may be fitted into one or more slots in the mount 14 and the length adjusted to accommodate variations in bias force required to hold the mask 16 biased against the patient's face. In certain embodiments, once the original adjustments are made, the support 18 may be left attached to the mount 14.

Figure 5:
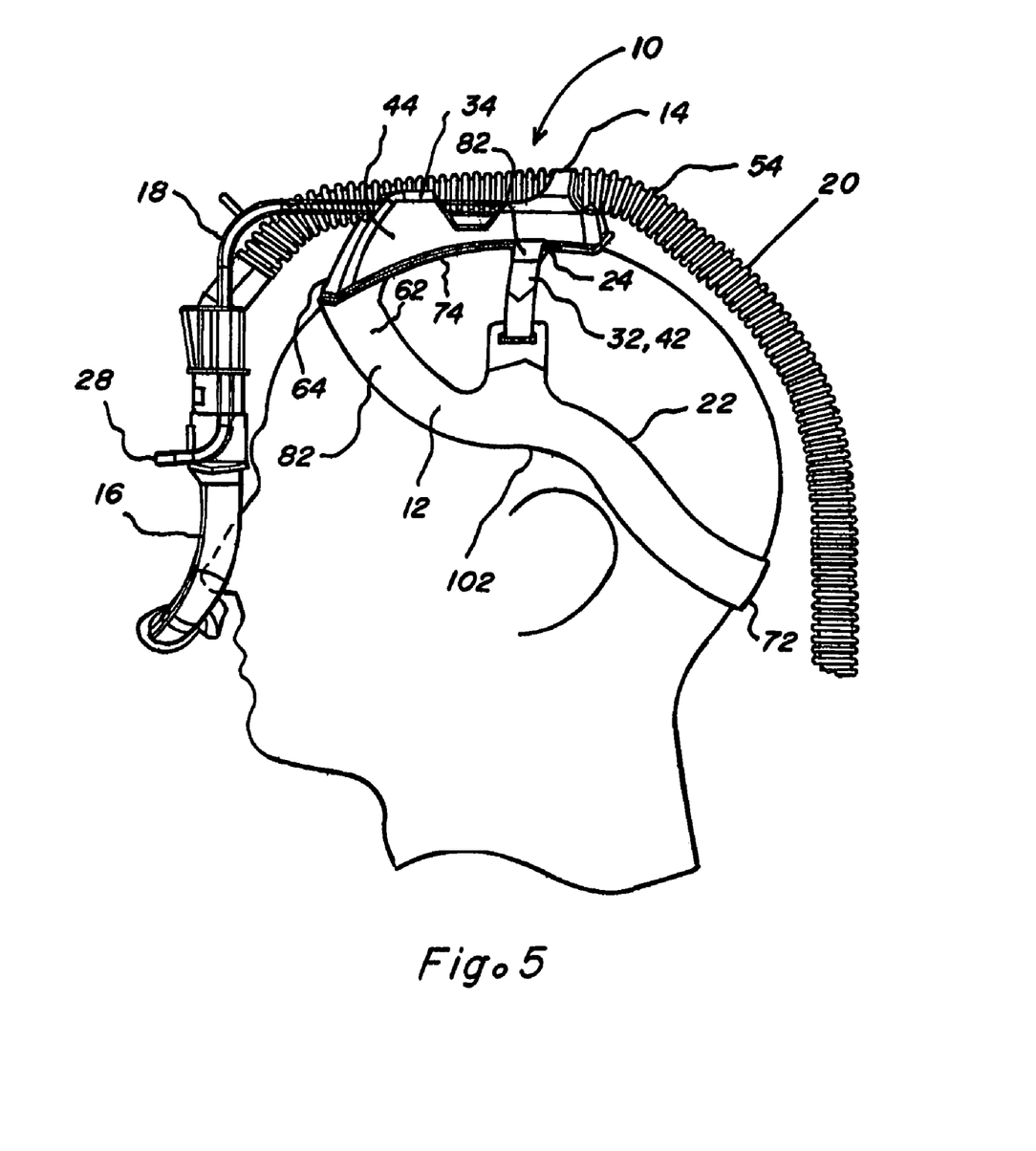
FIG. 5 illustrates a side view of an exemplary embodiment of a mask apparatus with nares seals in accordance with aspects of the present inventions.
Figure 6:
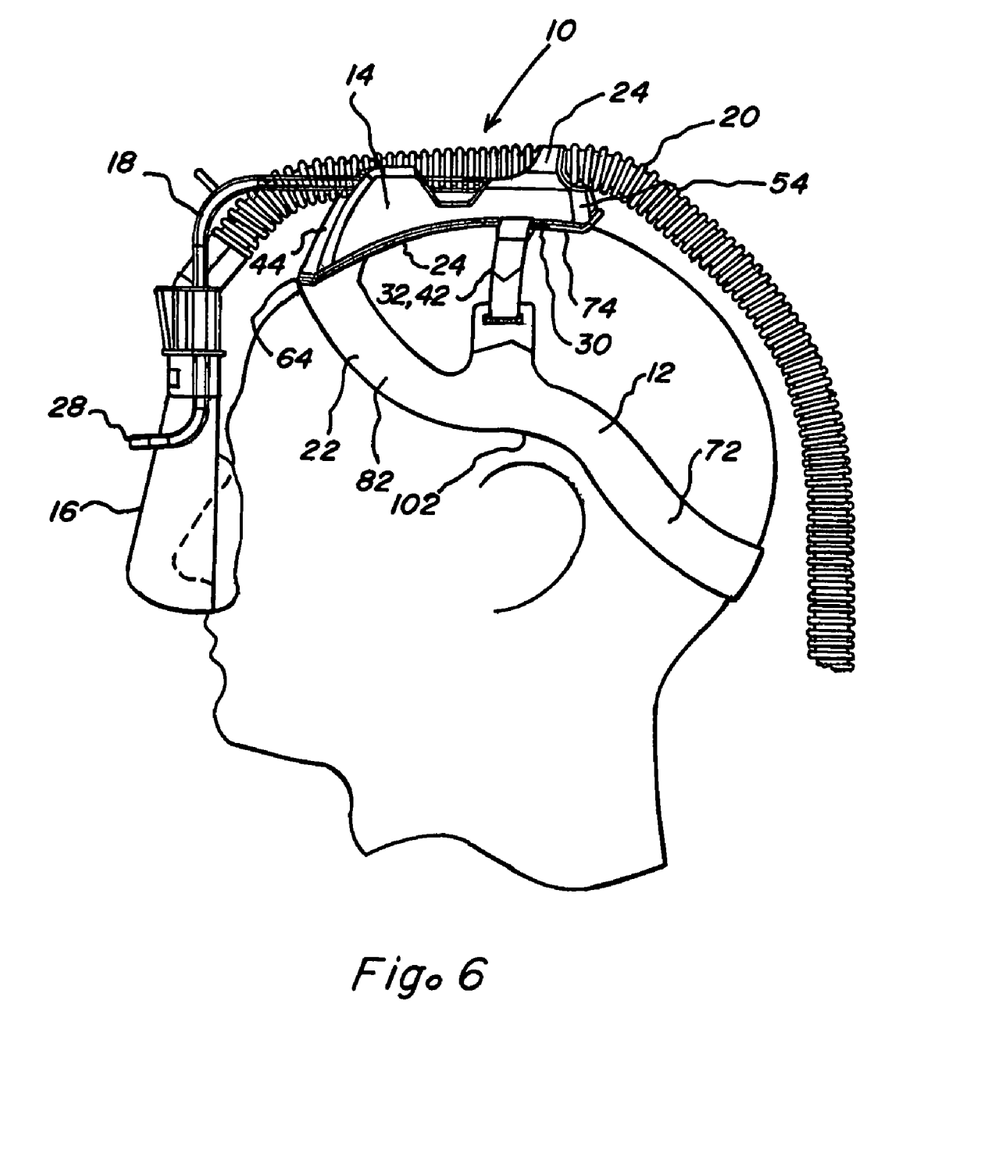
FIG. 6 illustrates a side view of an exemplary embodiment of a mask apparatus with a nasal mask in accordance with aspects of the present inventions.
Figure 7:
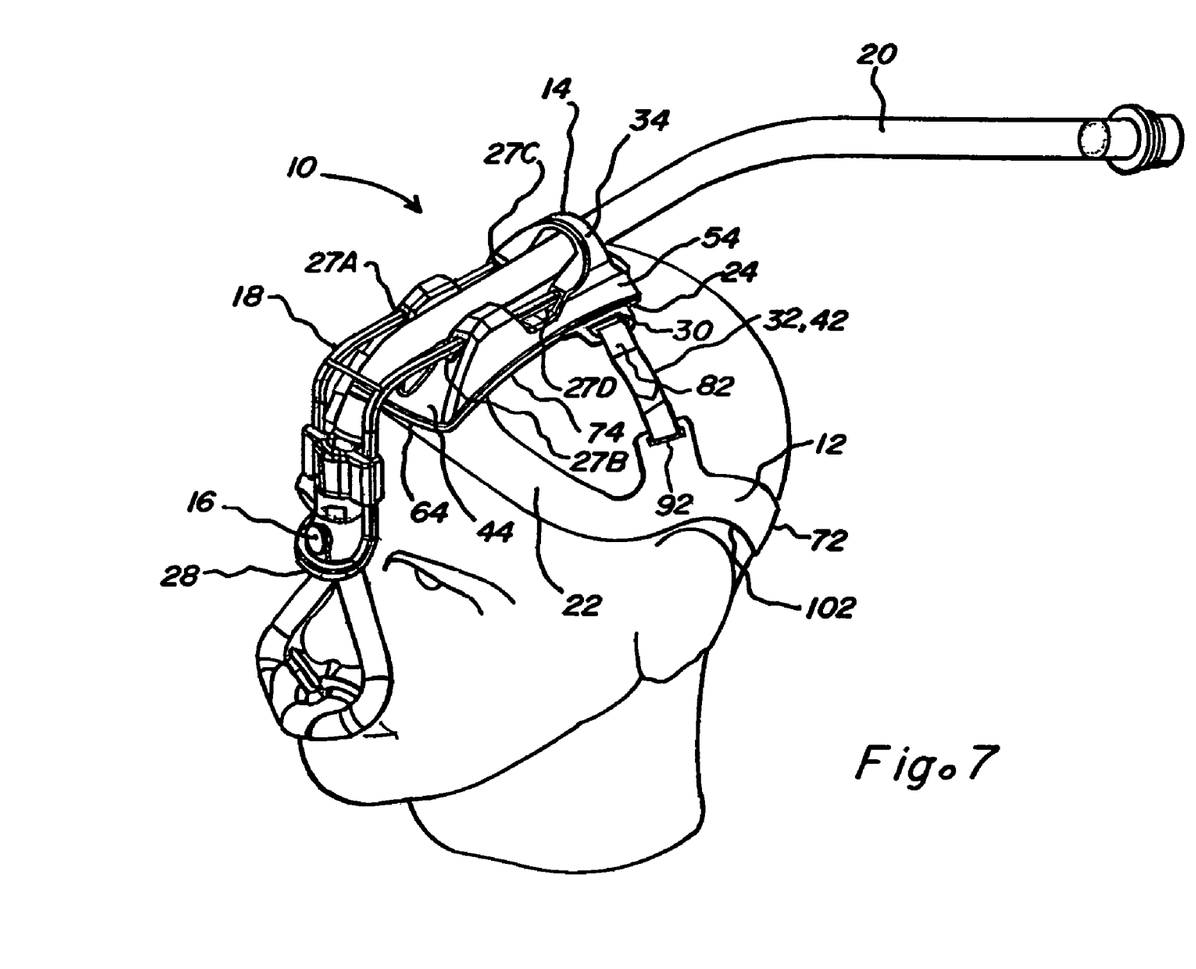
FIG. 7 illustrates a top view of an exemplary embodiment of a mask apparatus in accordance with aspects of the present inventions.

FIGS. 5 to 7 show exemplary embodiments of a mask apparatus 10. The illustrated embodiments include a circumferential band 22 encircling the head from the forehead just below the hair line to the inion protrusion of the occipital bone of a user for exemplary purposes. The circumferential band 22 in this embodiment may be configured to sit higher on the head of the user than in the embodiment of FIGS. 1 to 4. Therefore, an angle 102, in the form of an S-shaped curve, at approximately the level of the ear may prevent contact with the aspects of the ears. The lateral stabilizing band 32, 42 extends upward from approximately the area of the angle 102 to the crown of the head for exemplary purposes. The mount 14 may be positioned to extend between about the circumferential band 22 and the lateral stabilizing bands 32, 42. The mount 14 may rest on a base 74. The mount 14 may be attached to the lateral stabilizing bands 32, 42 through an attachment 30 on each side of the mount 14. As particularly illustrated in FIG. 7, the mount 14 may be provided with receiving slots 27A and 27B to secure the support 18 to the mount 14. Additional receiving slots 27C and 27D may also be provide in mount 14 to secure particular configurations of supports 18. Tube 20 extends along the top surface of the mount 14 and thence down along the support 18 to loop 28 around the plenum and/or the nasal mask 16. In one aspect, the plenum 56 may function to receive and vent air. The plenum 56 may be positioned at or about the loop 28 of the support 18. The loop 28 may pass around the plenum 56, rather than around the entire mask 16. This may afford sufficient biasing force because the preferred nasal mask may be lightly anchored in the nares of the user and may be light in weight.

Figure 8A:
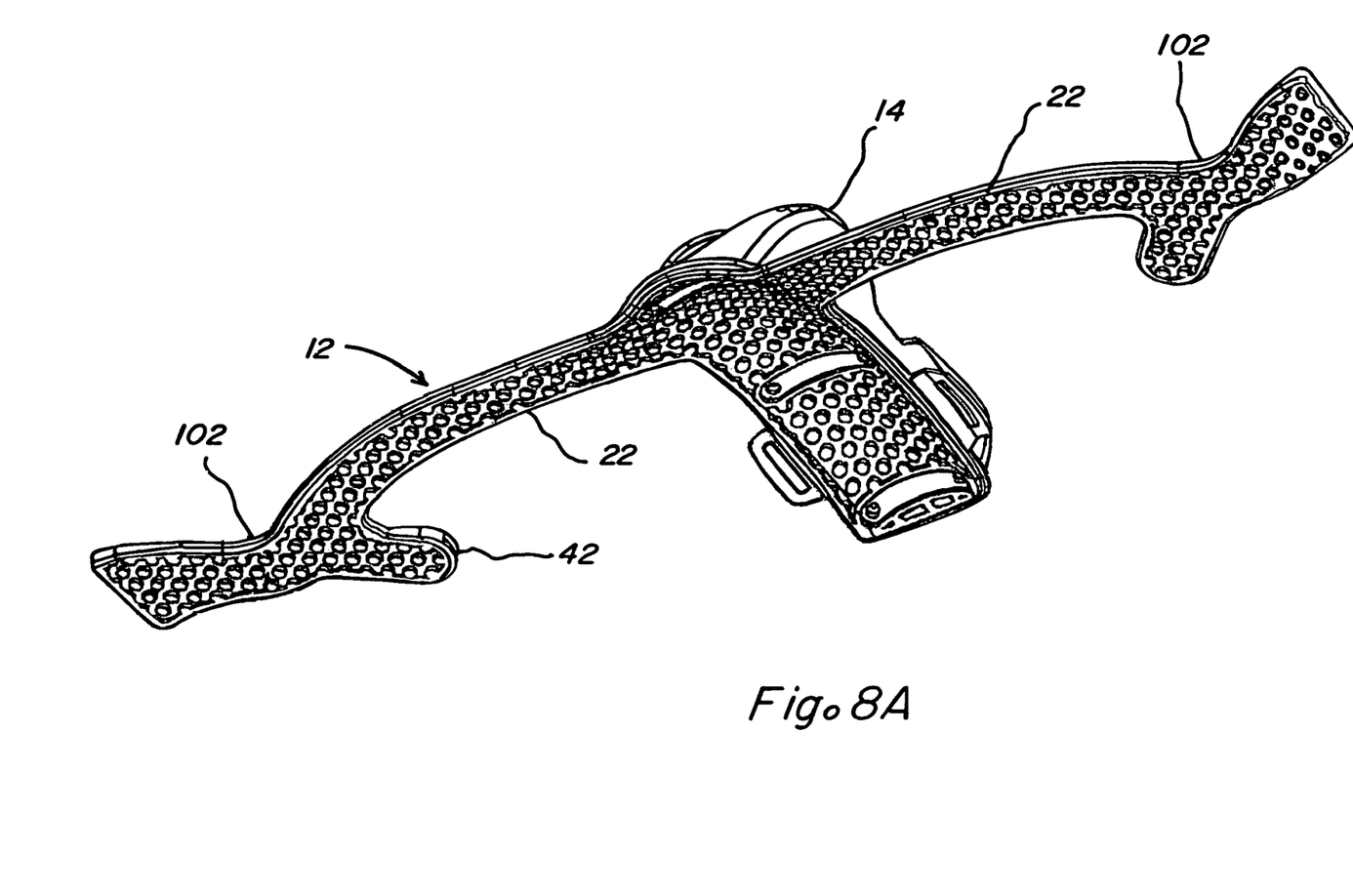
FIG. 8A illustrates perspective view showing various lower and inner surfaces of at least a portion of a mask apparatus in accordance with aspects of the present inventions.
Figure 8B:
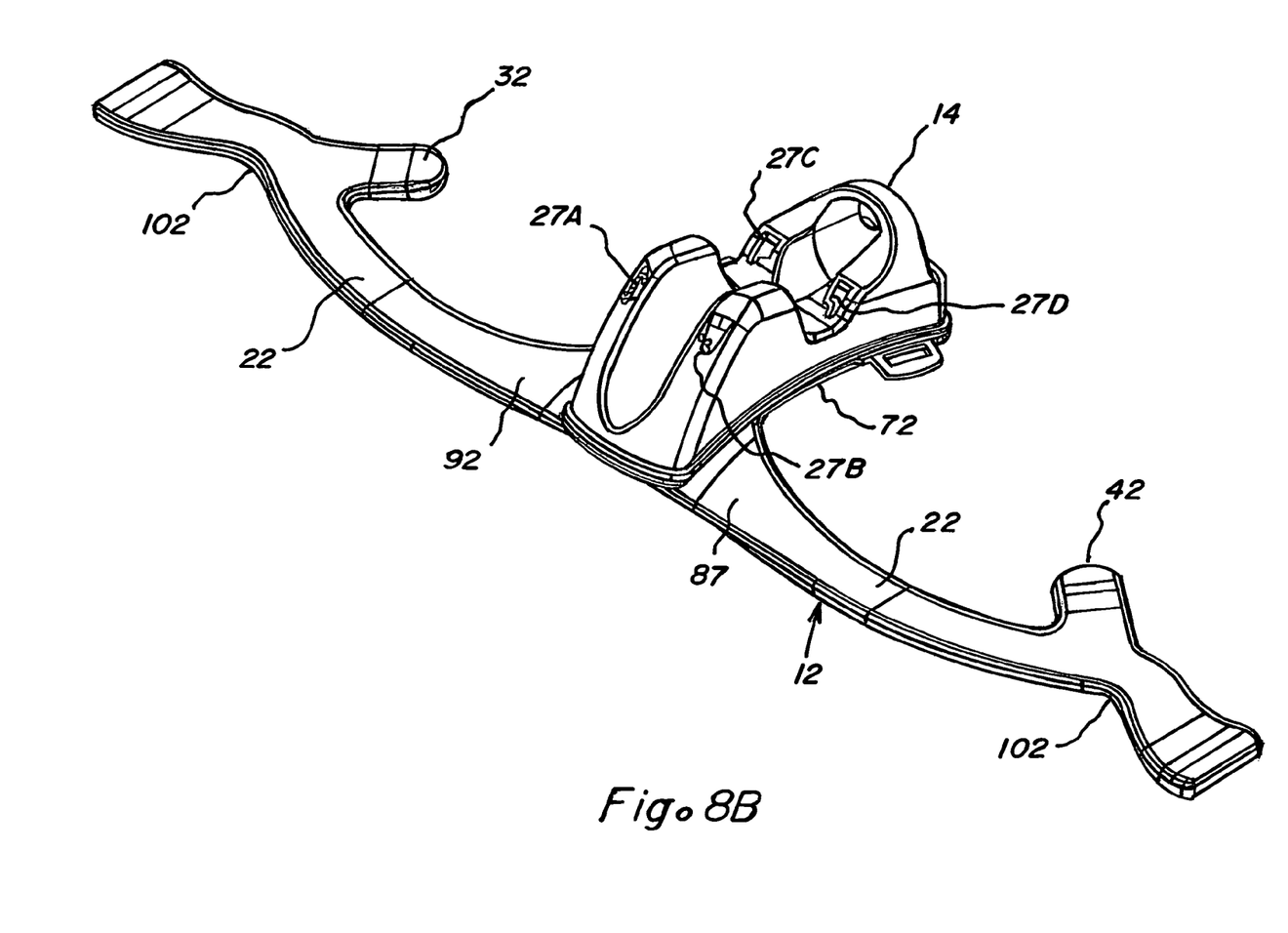
FIG. 8B illustrates a perspective view showing various upper and outer surfaces of at least a portion of a mask apparatus in accordance with aspects of the present inventions.

FIGS. 8A and 8B illustrate an exemplary embodiment of bands 12 and portions thereof that are molded into a unitary component which is secure to the mount 14. As illustrated, the mount 14 is secured over aspects of the circumferential band 22 and a base 74. When assembled, the ends of the circumferential band 22 may be attached securely to each other by sonic welding, adhesives, or other fixed bonding method, but preferably are attached using adjustable mechanisms, such as for example, buckles, snaps, or hook and loop type fasteners. Portions of the lateral stabilizing bands 32, 42 are shown molded as tongues of the circumferential band 22. The attachments may be formed on the mount 14 or on the outer substrate of the lateral stabilizing band 32, 42. Both the circumferential band 22 and the lateral stabilizing bands 32, 42 may be formed of an outer substrate that may be sufficiently firm to prevent the bands 12 from rolling, with an inner substrate of softer material on the side that contacts the skin and/or hair. An elastic and/or cushioning material may be provided between the inner substrate and the outer substrate. The bands 12 may be formed of any suitable materials or combinations of materials, such as for example, silicone/silicone foam or polyethylene/polyethylene foam.

Figure 9:
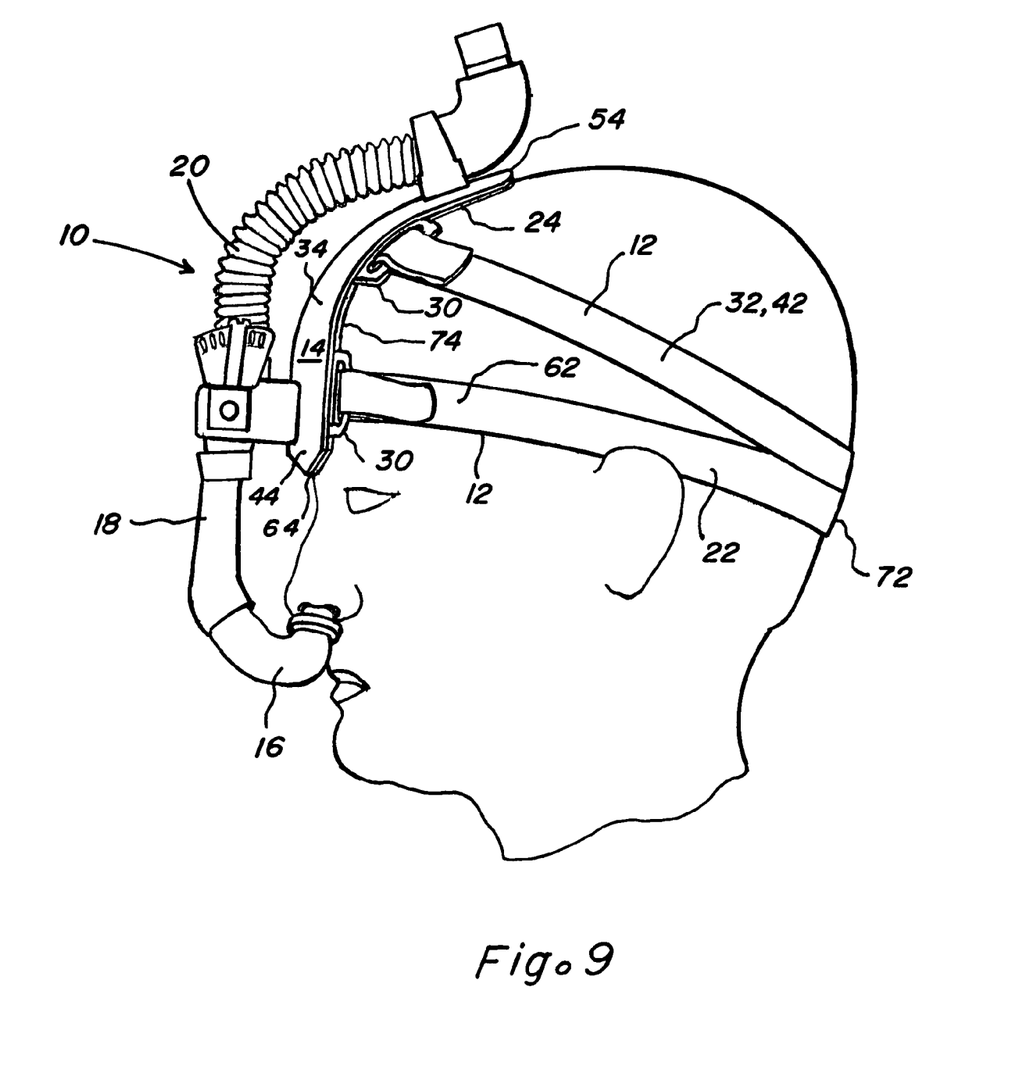
FIG. 9 illustrates a side view of another exemplary embodiment of a mask apparatus in accordance with aspects of the present inventions.

FIG. 9 illustrates another exemplary embodiment of a mask apparatus 10. The illustrated embodiment includes a circumferential band 22 encircling the head from the forehead to approximately the inion protrusion of the occipital bone of a user for exemplary purposes. As illustrated, the lateral stabilizing bands 32, 42 are a single band extending circumferentially about the head. As particularly illustrated, the lateral stabilizing bands 32, 42 extend from the top of the head to a location superior the circumferential band 22 on the occipital bone of a user for exemplary purposes. In one aspect, the lateral stabilizing bands 32, 42 may be secured to the circumferential band at a posterior portion of the circumferential band 22. In other aspects, the lateral stabilizing bands 32, 42 may be unsecured to the circumferential band and independently positionable about the head. The circumferential band 22 may be secured at or toward an anterior end 44 of the mount 14. The lateral stabilizing bands 32, 42 may be secured at or toward the posterior end 54 of the mount 14. The mount 14 may rest on a base 74. In certain aspects the mount 14 is secured to the base 74. The mount 14 may be attached to the circumferential band 22 and lateral stabilizing bands 32, 42 through attachments 30. The attachments 30 may include slots to receive the circumferential band 22 and lateral stabilizing bands 32, 42 through. The attachments 30 may be positioned on opposing sides of the mount 14. The mount 14 may be provided with receiving slots 27A and 27B to secure the support 18 to the mount 14. Additional receiving slots 27C and 27D may also be provide in mount 14 to secure particular configurations of supports 18. The tube 20 may be in fluid communication with a passage within a support 18. The mask 16 is also in fluid communication with the passage of support 18 to communicate air to a user. The support 18 cantilevers the mask from the anterior edge 64 of the mount 14.

The illustrated exemplary embodiment of a mask apparatus 10 in accordance with aspects of the present inventions may provide the force necessary to hold the mask 16 biased against the face. The forces may be transmitted from the top of the head and/or forehead to the nasal area or face via the mask 16 and/or support 18. It should be noted that the force will vary from user to user. The variables include:

higher or lower positive air pressure to hold the patient's airway open;

adequate flow to a user requiring breathing assistance;

a more restless user who tends to dislodge the mask;

a patient's personal preference; or an unusual topology of the patient's face.

By providing a lightweight, less restrictive mask apparatus 10 with sufficient adjustability in and between the mount 14, the mask 16, the support 18 when present, the circumferential band 22 and/or the lateral stabilizing bands 32, 42, most patients will find the apparatus in accordance with one or more aspects of the present inventions comfortable and will be encouraged to comply with its use.

In operation, a user secures positions the circumferential band 22 about the user's head. The user positions the mask 16 in communication with the user's airways. The user adjusts the circumferential band 22, the first lateral stabilizing band 32 and the second lateral stabilizing band 42 to permit adequate sealing of the mask 16 for the administration of a positive airway pressure therapy. The tube 20 is placed in communication with a blower configured to deliver pressurized air for positive airway pressure therapies. The positive airway pressure therapy may then be administered to the user.

It may be understood that following the teachings of this patent application, those skilled in the art to which it pertains may readily make insubstantial changes, which changes are considered to be within the spirit and scope of this invention.

What is claimed is:

1. A mask apparatus, comprising:

a mount having a lower surface adapted to conform to the shape of a portion of a head of a user;

a mask secured to the mount with the mask cantilevered from the mount;

a circumferential band secured to the mount toward an anterior end of the mount; the band adapted to extend around a majority of the circumference of the head of a user;

a first lateral stabilizing band and a second lateral stabilizing band, each of the first lateral stabilizing band and the second lateral stabilizing band defining a first end and a second end, the first end of the first lateral stabilizing band secured to the mount and the second end of the first lateral stabilizing band secured to the circumferential band, and the first end of the second lateral stabilizing band secured to the mount and the second end of the second lateral stabilizing band secured to the circumferential band.

2. A mask apparatus, as in claim 1, further comprising the mount having a leading edge and the mask extending from the leading edge of the mount.

3. A mask apparatus, as in claim 1, further comprising the circumferential band defining an angle between an anterior portion of the circumferential band and a posterior portion of the circumferential band.

4. A mask apparatus, comprising:

a mount;

a mask secured to the mount with the mask cantilevered from the mount;

a circumferential band secured to the mount toward an anterior end of the mount, the circumferential band adapted to extend around a majority of the circumference of the head of a user;

a first lateral stabilizing band and a second lateral stabilizing band, the first lateral stabilizing band and the second lateral stabilizing band defining a first end and a second end, the first end of the first lateral stabilizing band secured to the mount and the first end of the second lateral stabilizing band secured to the mount and the second end of the first lateral stabilizing band secured to the second end of the second lateral stabilizing band, the first lateral stabilizing band and the second lateral stabilizing band secured to one another to extend circumferentially about at least a portion of the head of a user.

* * * * *